United States Patent [19]

Hässlin et al.

[11] Patent Number: 5,006,161
[45] Date of Patent: Apr. 9, 1991

[54] HERBICIDAL COMPOSITION

[75] Inventors: Hans W. Hässlin, Grenzach-Wyhlen; Wolfgang P. Iwanzik, Sisseln, both of Switzerland

[73] Assignee: Ciba-Geigy Corporation, Ardsley, N.Y.

[21] Appl. No.: 162,534

[22] Filed: Mar. 1, 1988

[30] Foreign Application Priority Data

Mar. 6, 1987 [CH] Switzerland .......................... 849/87

[51] Int. Cl.$^5$ ...................... A01N 37/18; A01N 25/28
[52] U.S. Cl. ................................... 71/118; 71/DIG. 1
[58] Field of Search ............................. 71/DIG. 1, 118

[56] References Cited

U.S. PATENT DOCUMENTS

| | | | |
|---|---|---|---|
| 4,160,838 | 7/1979 | Van Keet et al. | |
| 4,230,809 | 10/1980 | Heinrich et al. | |
| 4,285,720 | 8/1981 | Scher. | |
| 4,303,548 | 12/1981 | Shimazaki et al. | |
| 4,319,918 | 3/1982 | Baltroschat et al. | 71/118 |
| 4,351,667 | 9/1982 | Chupp. | |
| 4,563,212 | 1/1986 | Becher et al. | |

FOREIGN PATENT DOCUMENTS

| | | | |
|---|---|---|---|
| 0113030 | 7/1984 | European Pat. Off. | |
| 0165227 | 12/1985 | European Pat. Off. | 71/DIG. 1 |
| 214936 | 3/1987 | European Pat. Off. | |

OTHER PUBLICATIONS

Lasso ® Micro-Tech ®, 115-85-L02, 9 pages.
Springer-Verlag Heidelberg New York, vol. 8, pp. 90–93 & 322–327 (1982).

*Primary Examiner*—Glennon H. Hollrah
*Assistant Examiner*—John Pak
*Attorney, Agent, or Firm*—Edward McC. Roberts

[57] ABSTRACT

Herbicidal compositions in the form of microcapsules are described which microcapsules have a capsule wall of polyurea and encapsulate a herbicidally active N-chloroacetylcyclohexeneamine or a mixture of a herbicidally active N-chloroacetylcyclohexeneamine and a herbicidally active chloroacetanilide.

12 Claims, No Drawings

HERBICIDAL COMPOSITION

The present invention relates to herbicidal compositions in the form of aqueous suspensions of microcapsules enclosing a herbicidally active N-chloroacetylcyclohexeneamine or a mixture of a herbicidally active N-chloroacetylcyclohexeneamine and herbicidally active chloroacetanilide.

Herbicidally active N-chloroacetylcyclohexeneamines are known from U.S. Pat. No. 4,351,667 and European patent specification No. EP-A-0 113 030. In conventional formulations, such as emulsifiable concentrates, these compounds show a pronounced initial activity. However, their long term activity is unsatisfactory.

Herbicidally active haloacetanilides are known from R. Wegler, Chemie der Pflanzenschutz- und Schädlingsbekämpfungsmittel, Vol. 8, Springer Verlag, Heidelberg-New York, 1982, pages 90–93 and 322–327.

Well known compounds of this class are N-chloroacetyl-N-(2-methoxy-1-methylethyl)-2-ethyl-6-methylaniline (Metolachlor) and N-chloroacetyl-N-methoxymethyl-2,6-diethylaniline (Alachlor).

It is known to improve the long term activity of agrochemicals by application of specific formulation techniques. For example an active ingredient can be absorbed on porous carriers from which it is slowly released. Further, it is known to enclose active substances into microcapsules having a capsule wall consisting of polymeric material, such as polyurea. From these microcapsules the active ingredient is slowly released by diffusion through the capsule wall. A desired rate of release can be adjusted by the thickness of capsule wall and by the choice of an appropriate wall-forming material. This microencapsulation technique is generally suitable to ensure a satisfactory long term activity of an active substance. However, a considerable and sometimes drastic loss of initial activity has to be accepted according to common experience. This is particularly true for haloacetanilides which when encapsulated into microcapsules having a wall of polyurea show only a poor initial activity.

It is the object of the present invention to provide herbicidal compositions containing a herbicidally active N-chloroacetylcyclohexeneamine as active ingredient and having satisfactory initial and long term activity.

It has been found that N-chloroacetylcyclohexeneamines encapsulated into microcapsules having a capsule wall of polyurea show satisfactory initial and long term activity which is superior to that of other formulations containing herbicidally active N-chloroacetylcyclohexeneamins, such as emulsifiable concentrates and wettable powders.

Accordingly, the present invention provides herbicidal compositions which comprise an aqueous suspension of microcapsules having a capsule wall of polyurea and encapsulating a herbicidally active N-chloroacetylcyclohexeneamine of the formula I

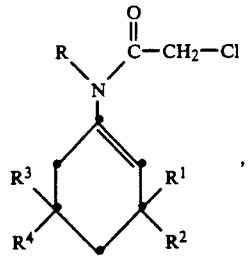

wherein R is $C_1$–$C_6$-alkyl or $C_3$–$C_6$-alkenyl and $R^1$, $R^2$, $R^3$ and $R^4$ independently from each other are hydrogen or $C_1$–$C_4$-alkyl.

Preferred N-chloroacetylcyclohexeneamines of the formula I are those wherein R is $C_1$–$C_4$-alkyl or $C_3$–$C_6$-alkenyl and $R^1$, $R^2$, $R^3$ and $R^4$ independently from each other are hydrogen or methyl.

Particularly preferred N-chloroacetylcyclohexeneamins of the formula I are:
N-isopropyl-N-chloracetylcyclohex-1-eneamine, N-isopropyl-N-chloracetyl-3(5)-methylcyclohex-1-eneamine, N-isopropyl-N-chloracetyl-3,5,5(3)-trimethylcyclohex-1-eneamine (Trimexachlor) and N-isopropyl-N-chloracetyl-3,3,5,5-tetramethylcyclohex-1-eneamine.

The most preferred N-chloroacetylcyclohexene of the formula I is Trimexachlor.

If the two pairs of substituents attached to cyclohexene ring in position 3 and 5 are different the compound of formula I can exist in two isomeric forms according to the equilibrium shown below:

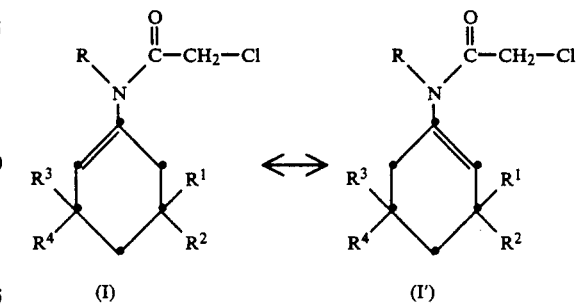

The present invention encompasses the isomers of formulae I and I' as well as all other isomers derivable from the meaning of the substituents R and $R^1$ to $R^4$ as defined above.

In the above definition of formula I $C_1$–$C_6$-alkyl encompasses methyl, ethyl, n-propyl, iso-propyl, n-butyl, iso-butyl, sec.-butyl, tert.-butyl and all isomers derivable from the pentyl and hexyl radicals.

The $C_3$–$C_6$-alkenyl groups are always bound through a $sp^3$-center. Preferred alkenyl groups are allyl, methallyl and 2-butenyl.

Aqueous suspensions of microcapsules having capsule wall of polyurea and enclosing a liquid substance which is insoluble or sparingly soluble in water can be prepared according to known processes by dissolving a polyisocyanate in the liquid substance to be encapsulated, dispersing the solution thus obtained in water and reacting the dispersion with an aqueous solution of polyamine. In such a process the capsule wall is formed by interfacial reaction of the polyisocyante dissolved in the dispersed or organic phase with the polyamine present in the continuous aqueous phase. The dispersion in water of the solution of the polyisocyanate in the substance to be encapsulated as a rule is carried out in the presence of one or more dispersing agents, such as polyvinyl alcohol, gelatine, and methyl cellulose (c.f. U.S. Pat. No. 3,577,515), salts of ligninsulfonic acid (c.f. U.S. Pat. Nos. 4,280,833 and 4,417,916), or combination of dispersing agents, for example a combination of an anionic dispersant, such is a salt of a polystyrenesulfonic acid, a salt of polyvinylsulfonic acid, a salt of a condensate of naphthalenesulfonic acid with formaldehyde or salts of a condensate of naphthalenesulfonic acid with phenolsulfonic acid and formaldehyde and a nonionic dispersant, such as polyvnyl alcohol, polyvinyl methyl ether, polyvinylpyrrolidone, hydroxyethyl cellulose, hydroxypropyl cellulose, methyl cellulose, alkylpolyethyleneglycol ethers, alkylphenolpolyglycol ethers, styrylphenolpolyglycol ethers, polyethylene oxides and polyethylenoxide-polypropyleneoxide block polymers (c.f. U.S. Pat. application Ser. No. 776,080, filed Sept. 13, 1985, or the corresponding European patent application No. EP-A-0 214 936). The processes described in the afore-mentioned reference are not limited to the encapsulation of liquid substances. Solid substances can also be encapsulated as solutions in an appropriate water-imiscible solvent.

The aqueous suspensions of microcapsules of this invention can be prepared according to the processes described in the afore-mentioned references. Solid N-chloroacetylcyclohexeneamins, for example Trimexachlor, are advantageously encapsulated as solutions in a water-imiscible solvent. In many cases the polyisocyanate used as reactive component for the formation of the capsule wall can serve as solvent which together with the solid N-chloroacetylcyclohexeneamine forms a liquid capable of being dispersed in water and subsequently reacted with a polyamine. Preferably, however, an additional water-imiscible solvent, such as an aliphatic or aromatic hydrocarbon, a cyclic ketone or a halogenated hydrocarbon.

Solvents which can be used for this purpose are, for example, hexane, cyclohexane, benzene, toluene, xylene, mineral oil, kerosene, cyclohexanone, methylene chloride, chloroform, chlorobenzene and o-dichlorobenzene. The mixtures of mono- and polyalkylated aromatics commerically available under the registered trade mark SHELLSOL ® are also suitable. The use of these solvent is also favourably in cases where polyisocyanate is insoluble or only sparingly soluble in the substance to be encapsulated. Further, by the use of a water-imiscible solvent the release rate of the herbicide can be influenced and the solvent has also an antifreezing effect. As rule 0.25-0.75 parts per weight of solvent can be used per part of N-chloroacetylcyclohexeneamine of the formula I.

Apart from the afore-mentioned advantages the use of an additional solvent is also accompanied by a certain disadvantage because the additional solvent which is encapsulated together with the active compound reduces the amount of active compound which can be encapsulated into a capsule of a given size. It has now been found that the solvent used for the encapsulation of solid N-chloroacetylcyclohexeneamines of the formula I can be totally or partially replaced by a herbicidally active haloacetanilide.

Accordingly, the present invention also provides herbicidal compositions which comprise an aqueous suspension of microcapsules having a capsule wall of polyurea and encapsulating a mixture of a herbicidally active N-chloroacetylcyclohexeneamine of the formula I

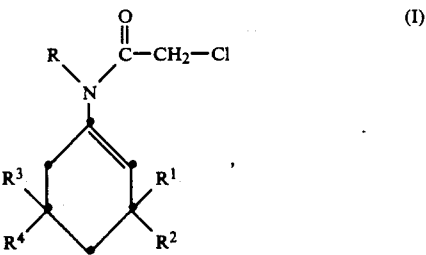

wherein R is $C_1$–$C_6$-alkyl or $C_3$–$C_6$-alkenyl and $R^1$, $R^2$, $R^3$ and $R^4$ independently from each other are hydrogen or $C_1$–$C_4$-alkyl and a herbicidally active chloroacetanilide of the formula II

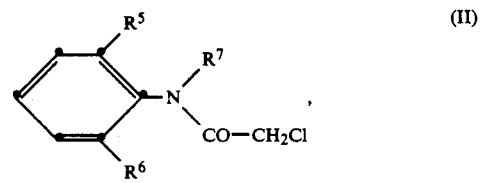

wherein $R^5$ and $R^6$ independently from each other are hydrogen, halogen, methyl or ethyl and $R^7$ represents $C_1$–$C_4$-alkoxymethyl, 2-($C_1$–$C_4$-alkoxy)-ethyl or 2-($C_1$–$C_4$-alkoxy)-1-methylethyl, the per weight ratio of the N-chloroacetylcyclohexeneamine of the formula I to the chloroacetanilide of the formula II being within the range of 2:1 to 1:2.

Preferably, the per weight ratio of the N-chloroacetylcyclohexeneamine of the formula I to the N-chloroacetanilide of the formula II is about 1:1.

Suitable chloroacetanilide of the formula II are:
N-chloroacetyl-N-ethoxymethyl-2-ethyl-6-methylaniline,
N-chloroacetyl-N-methoxymethyl-2,6-diethylaniline (Alachlor),
N-chloroacetyl-N-(2-methoxyethyl)-2,6-dimethylaniline (Dimethachlor),
N-chloroacetyl-N-(2-n-propoxyethyl)-2,6-dimethylaniline,
N-chloroacetyl-N-(2-isopropoxyethyl)-2,6-dimethylaniline,
N-chloroacetyl-N-(2-methoxyethyl)-2-ethyl-6-methylaniline,
N-chloroacetyl-N-(methoxyethyl)-2,6-diethylaniline,
N-chloroacetyl-N-(2-ethoxyethyl)-2-ethyl-6-methylaniline,
N-chloroacetyl-N-(2-methoxy-1-methylethyl)-2-methylaniline,
N-chloroacetyl-N-(2-methoxy-1-methylethyl)-2,6-dimethylaniline,
N-chloroacetyl-N-(2-methoxy-1-methylethyl)-2,6-diethylaniline,
N-chloroacetyl-N-(2-methoxy-1-methylethyl)-2-ethyl-6-methylaniline (Metolachlor),
N-chloroacetyl-N-(2-ethoxyethyl)-2,6-diethylaniline,
N-chloroacetyl-N-(2-n-propoxyethyl)-2-ethyl-6-methylaniline,
N-chloroacetyl-N-(2-propoxyethyl)-2,6-diethylaniline,
N-chloroacetyl-N-(2-isopropoxyethyl)-2-ethyl-6-methylaniline,
N-chloroacetyl-N-(2-ethoxyethyl)-2-methylaniline, 2-chloroacetyl-N-(2-methoxyethyl)-2-methylaniline,
N-chloroacetyl-N-(2-methoxy-2-methylethyl)-2,6-dimethylaniline,
N-chloroacetyl-N-(1-ethyl-2-methoxyethyl)-2,6-dimethylaniline,
N-chloroacetyl-N-(2-ethoxyethyl-1-methylethyl)-2,6-dimethylaniline,
N-chloroacetyl-N-(2-methoxyethyl)-2-chlor-6-methylaniline,
N-chloroacetyl-N-(2-ethoxyethyl)-2-chlor-6-methylaniline,
N-(n-butoxymethyl)-N-chloroacetyl-2,6-diethylaniline and
N-(2-n-butoxyethyl)-N-chloroacetyl-2,6-diethylaniline.

Preferred chloroacetanilides of the formula II are those which form liquids when they are intimately mixed with an N-chloroacetylcyclohexeneamine of the formula I. Particularly preferred chloroacetanilides of the formula II are those which are liquid at normal temperature. The most preferred compound of this kind is Metolachlor. With the use of chloroacetanilides of the formula II which form liquids when they are intimately mixed with a N-chloroacetylcyclohexeneamine of the formula I or which are liquids themselves no additional solvent is necessary. With the use of other chloroacetanilides of the formula II which are solids themselves the amount of solvent can be reduced considerably. In this way it is possible to produce microcapsules containing an increased amount of active substance.

Preferred herbicidal compositions according to the invention are aqueous suspensions of microcapsules having a capsule wall of polyurea and encapsulating a mixture of N-isopropyl-N-chloroacetyl-3,5,5(3)-trimethylcyclohex-1-ene-amine(Trimexachlor) and N-chloroacetyl-N-(2-methoxy-1-methylethyl)-2-ethyl-6-methylaniline(Metolachlor).

The aqueous capsule suspensions according to the present invention are prepared by dissolving a polyisocyanate in a N-chloroacetylcyclohexeneamine of the formula I or in a mixture of a N-chloroacetylcyclohexeneamine of the formula I and N-chloroacetanilide of the formula II, dispersing the solution thus obtained in water in the presence of one or more dispersing agents and reacting the dispersion with an aqueous solution of the polyamine.

Suitable polyisocyanates in general are those compounds that contain two or more isocyanate groups in the molecule. Preferred isocyanates are di-and triisocyanates whose isocyanate groups may be linked to an aliphatic or aromatic moiety. Examples of suitable aliphatic diisocyanates are tetramethylene diisocyanate, pentamethylene diisocyanate and hexamethylene diisocyanate. Suitable aromatic isocyanates are toluylene diisocyanate (TDI: mixture of 2,4- and 2,6-isomers), diphenylmethane-4,4'-diisocyanate (MDI: DESMODUR ® VL, Bayer), (polymethylene polyphenylisocyanate (MONDUR ® MR, Mobay Chemical Company); PAPI ®, PAPI ® 135 (Upjohn Co.), 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4',4''-triphenylmethane triisocyanate. A further suitable diisocyanate is isophorone diisocyanate. Also suitable are adducts of diisocyanates with polyhydric alcohols such as ethylene glycol, glycerol and trimethylolpropane, obtained by addition, per mole of polyhydric alcohol, of a number of moles of diisocyanate corresponding to the number of hydroxyl groups of the respective alcohol. In this way several molecules of diisocyanate are linked through urethane groups to the polyhydric alcohol to form high molecular polyisocyanates. A particularly suitable product of this kind (DESMODUR ® L) can be prepared by reacting 3 moles of toluylene diisocyanate with 1 mole of 2-ethylglycerol (1,1-bismethylolpropane). Further suitable products are obtained by addition of hexamethylene diisocyanate or isophorone diisocyanate with ethylene glycol or glycerol. Preferred polyisocyanates are diphenylmethane-4,4'-diisocyanate and polymethylene polyphenylisocyanate.

The di- and triisocyanates specified above can be employed individually or as mixtures of two or more such isocyanates.

Suitable polyamines in general are those compounds that contain two and more amino groups in the molecule, which amino groups may be linked to aliphatic and aromatic moieties. Examples of suitable aliphatic polyamines are α,ω-diamines of the formula

wherein n is an integer from 2–6. Exemplary of such diamines are ethylenediamine, propylene-1,3-diamine, tetramethylenediamine, pentamethylenediamine and hexamethylenediamine. A preferred diamine is hexamethylenediamine.

Further suitable aliphatic polyamines are polyethylenimines of the formula

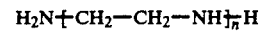

wherein n is an integer from 2 to 5. Representative examples of such polyethylenimines are: diethylenetriamine, triethylenetriamine, tetrathylenepentamine, pentaethylenehexamine.

Further suitable aliphatic polyamines are dioxaalkane-α, ω-diamines such as 4,9-dioxadodecane-1,12-diamine of formula

Examples of suitable aromatic polyamines are 1,3-phenylenediamine, 2,4-toluylenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraaminoanthraquinone. Those polyamines which are insoluble or insufficiently soluble in water may be used as hydrochlorides.

Yet further suitable polyamines are those that contain sulfo or carboxyl groups in addition to the amino groups. Examples of such polyamines are 1,4-phenylenediaminesulfonic acid, 4,4'-diaminodiphenyl-2-sulfonic acid, or diaminomonocarboxylic acids such as ornithine and lysine.

The above polyamines may be used individually or as mixtures of two or more polyamines.

Polyamines used for polycondensation may also be generated in a process known per se by reacting an appropriate polyisocyanate with water followed by decarboxylation of the carbamic acid formed.

Suitable solvents (cosolvents) in which the N-chloroacetylcyclohexeneamines of the formula I or mixtures of a N-chloroacetylcyclohexene of the formula I and a N-chloroacetanilide of the formula I may be dissolved are aliphatic and aromatic hydrocarbons such as hexane, cyclohexane, benzene, toluene, xylene, mineral oil or kerosene. Also suitable are cyclohexanone, as well as halogenated hydrocarbons such as methylene chloride, chloroform, chlorobenzene and o-dichlorobenzene. The mixtures of mono- and polyalkylated aromatics commercially available under the registered trademark SHELLSOL ® are also suitable.

With the general process discribed above microcapsules are obtained having a wall of polyurea. According to a variation of this process microcapsules can be prepared having a wall of polyurea which contains up to 30% of a polyamide. According to this variation up to 30% of the molar amount of polyisocyanate required for the formation of the capsule wall is replaced by the corresponding amount of an acid chloride of a dior polycarboxylic acid. Suitable acid chlorides are, for example, adipic acid dichloride, maleic acid dichloride, sebacid acid dichloride and succinic acid dichloride. These acid chlorides can be dissolved together with the polyisocyanate in a N-chloroacetylcyclohexeneamine of the formula I or in a mixture of a N-chloroacetylcyclohexeneamine of the formula I and a N-chloroacetanilide of the formula II optionally in the presence of an additional water-imiscible solvent.

The preparation of the aqueous suspensions of microcapsules is advantageously carried out in the presence of one or more dispersants. Suitable dispersants are anionic and nonionic dispersants. Preferably the aqeous suspensions of microcapsules of this invention are prepared according to the process described in the European Patent Application No. EP-A-0 214 936 in the presence of an anionic dispersant and of at least one nonionic protective coloid and/or a nonionic surfactant.

Suitable anionic dispersants are in general oligomers and polymers, as well as polycondensates, which contain a sufficient number of anionic groups to ensure their water-solubility. Examples of suitable anionic groups are sulfo groups or carboxyl groups; but polymers containing carboxyl groups can only be used in the higher pH range, preferably at a pH higher than 5. The number of anionic groups per polymer molecule is usually at least 60% of the number of monomer units contributing to the structure of the molecule. Oligomers and polymers that contain sulfo groups can be prepared either by polymerising monomers that contain sulfo groups or by sulfonating the appropriate oligomers or polymers. Polymers that contain carboxyl groups can be obtained by saponifying polyacrylates or polymethacrylates, in which case the degree of saponification must be at least 60%. Particularly suitable anionic dispersants are sulfonated polymers and condensates of aromatic sulfonic acids with formaldehyde. Typical examples of such anionic dispersants are:

A. Salts of polystyrenesulfonic acid, in particular the alkali metal, alkaline earth metal and ammonium salts, and the salts of organic amines which can be obtained by polymerising styrenesulfonic acid or salts thereof or by sulfonation of polystyrene and subsequent neutralisation with a suitable base, in which latter case the degree of sulfonation must be at least 60%;

B. Salts of polyvinylsulfonic acid, in particular the alkali metal, alkaline earth metal and ammonium salts, and the salts with organic amines which can be obtained by polymerising vinylsulfonic acid or salts therof;

C. Salts of condensates of naphthalenesulfonic acids, preferably naphthalene-2-solfonic acid, with formaldehyde, in particular the alkali metal, alkaline earth metal and ammonium salts, and salts of thereof with organic amines which can be obtained by sulfonation of naphthalene, condensation of the resultant naphthalenesulfonic acids with formaldehyde, and neutralisation with a suitable base. The condensates may be represented by the formula

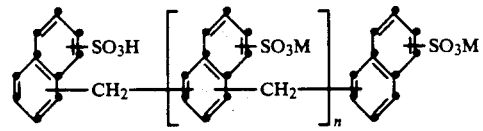

wherein M is sodium, potassium, magnesium, calcium, ammonium or the cation derived from an organic amine, and n is 1 to 25. The molecular weight of these compounds is in the range from about 500 to 6000.

D. Salts of condensates of naphthalenesulfonic acid with phenolsulfonic acid and formaldehyde, in particular the alkali metal, alkaline earth metal and ammonium salts, and salts with organic amines. These products are sulfo group containing polymers with an average molecular weight of 6000 to 8000, in which the momomer units naphthalene and phenol are linked to each other partly through methylene groups and partly through sulfo groups. Their approximate structure is:

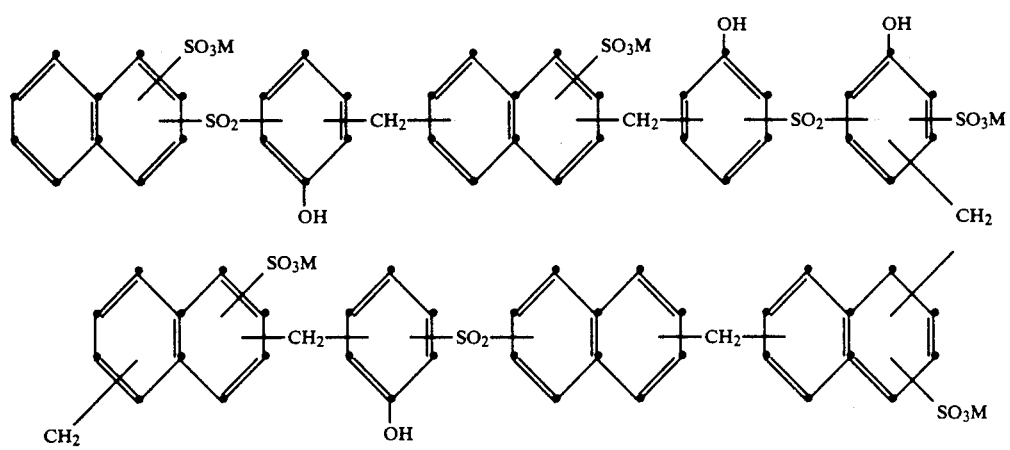

-continued

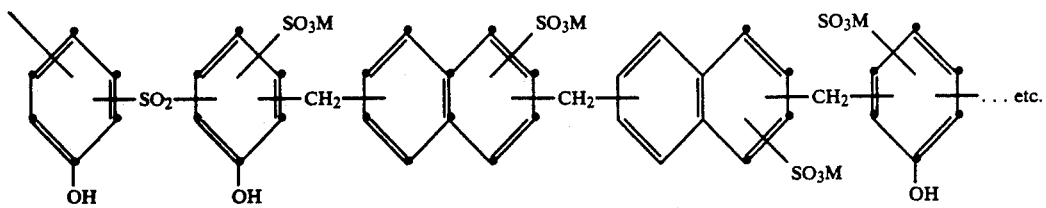

wherein M is sodium, potassium, magnesium, calcium, ammonium or the cation derived from an organic amine.

E. Salts of ligninsulfonic acid, in particular the sodium, potassium, magnesium, calcium or ammonium salt.

Preferred anionic dispersants are salts of polystyrenesulfonic acid (type A), salts of condensates of naphthalenesulfonic acid with formaldehyde (type C) and, in particular, condensates of naphthalenesulfonic acid with phenolsulfonic acid and formaldehyde (type D).

The condensates of naphthalenesulfonic acid with phenolsulfonic acid and formaldehyde of type D, which are especially preferred anionic dispersants, have so far not been described in the literature. They can be prepared by converting naphthalene, at 120°-130° C., first with concentrated sulfuric acid and/or oleum into naphthalenesulfonic acid, then adding phenol to the reaction mixture, and carrying out further reaction initially at 120°-130° C. and then removing the water of reaction in vacuo at 150°-170° C. and condensing the reaction product with formaldehyde after cooling to 90°-100° C., then neutralising the reaction mixture to pH 6–7 and evaporating it to dryness and granulating the residue, affording a water-soluble anionic dispersant (hereinafter referred to as "dispersant A") in granular form with an average molecular weight of 6000 to 8000.

The sulfonation of naphthalene under the above specified conditions yields mainly naphthalene-2-sulfonic acid together with insignificant amounts of naphthalenedisulfonic acid. Upon addition of phenol, this is also sulfonated. However, in this process, in particular when subsequently heating to 150°-170° C., large amounts of sulfones such as 4,4'-dihydroxydiphenylsulfone and 4-hydroxyphenylnaphthylsulfone are also formed in addition to phenolsulfonic acid. Hence a polymer whose monomer units naphthalene and phenol are linked partly through methylene groups and partly through sulfo groups is formed in the subsequent condensation with formaldehyde. In the preparation of dispersant A, naphthalene, phenol, sulfuric acid, formaldehyde and base may be used in the molar ratio of 1:0.5–1:2–2.5:0.4–0.8:2–3. The molar ratio of naphthalene:phenol:sulfuric acid: formaldehyde:base is conveniently 1:0.7:2:0.5:2, with sodium hydroxide being advantageously used as base. The sulfuric acid consists advantageously of mixtures of concentrated sulfuric acid and oleum, with the amount of free SO₃ in the oleum being at least equivalent to the amount of water in the concentrated sulfuric acid, so that at least 100% sulfuric acid is formed when mixing concentrated sulfuric acid and oleum. Formaldehyde is conveniently used as aqueous solution, for example as 37% aqueous solution. The separation of the water of reaction by distillation is advantageously effected under a pressure of 10–50 bar.

Suitable nonionic protective colloids are in general water-soluble polymers whose molecular weight is normally in the range from 10,000 to 200,000. The average diameter of the capsules can be influenced by the molecular weight of the respective polymer employed. The use of water-soluble polymers of low molecular weight results in a lower viscosity of the reaction mixture and thus in the formation of larger capsules, whereas the use of water-soluble polymers of high molecular weight leads to a higher viscosity of the reaction mixture and therefore to the formation of capsules of smaller diameter. Examples of suitable water-soluble polymers are: polyvinyl alcohol, polyvinyl methyl ether, polyvinylpyrrolidone, hydroxyethyl cellulose, hydroxypropyl cellulose, methyl cellulose (degree of substitution: 1.5–2), hydroxyethylmethyl cellulose, hydroxypropylmethyl cellulose, poly(2-hydroxyethyl)methacrylate, poly[2-(2-hydroxyethoxy)-ethyl]methacrylate, polyethylene oxide (polyoxyethylene) and polyallyl alcohol (polyglycidol).

A preferred nonionic protective colloid is polyvinyl alcohol. Particularly preferred are polyvinyl alcohols with a viscosity of 4–60 cp (measured in 4% aqueous solutions at 20° C), which have been prepared by saponification of polyvinyl acetate, with the degree of saponification being at least 60%, but preferably 80–90%. Suitable products of this kind are those commercially available under the registered trademark MOWIOL ®.

Suitable nonionic surfactants are in general nonionic water-soluble polymers having an average molecular weight of below 20,000. Particularly suitable nonionic surfactants of this kind are the products which can be obtained by reaction of ethylene oxide, or by the combined reaction of ethylene oxide and propylene oxide, with fatty alcohols, alkylphenols, fatty acids, fatty acid esters of polyhydroxy compounds, fatty acid amides and fatty amines, where the number of ethylene oxide and propylene oxide units may vary within wide limits. In general, the number of ethylene oxide units or ethylene oxide and propylene oxide units is from 1–200, preferably from 5–100 and, most preferably, from 8–40. Examples of suitable nonionic surfactants are:

alkylpolyethylene glycol ethers of the formula

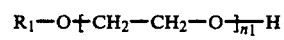

wherein $R_1$ is $C_8$–$C_{20}$alkyl and $n_1$ is 2–100. Products of this kind are commercially available under the registered trademarks BRIJ ® (Atlas Chemical), ETHYLAN ® CD and ETHYLAN ® D (Diamond Shamrock), GENAPOL ® C, GENAPOL ® O and GENAPOL ® S (Hoechst AG);

alkylphenol polyethylene glycol ethers of the formula

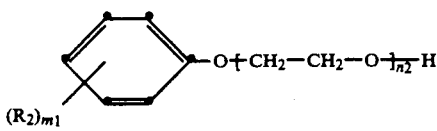

wherein $R_2$ is $C_8$-$C_{12}$alkyl, $m_1$ is 1 to 3 and $n_2$ is 2 to 40. Preferred meanings of $R_2$ are octyl and nonyl. Products of this kind are commerically available, for example under the registered trademarks Antarox (GAF), TRITON® X (Röhm and Haas Co.), ATLOX® 4991 (ICI), ARKOPAL® N (American Hoechst) und ETHYLAN® (Lankro Chem. Ltd);

α-phenethylphenol polyglycol ethers of the formula

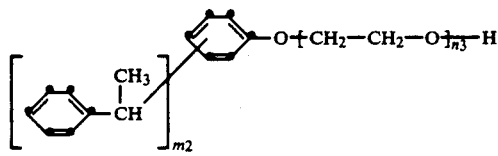

wherein $m_2$ is 1 to 3 and $n_3$ is 5 to 40. These products are designated ethoxylated styryl phenols. Commercially available products of this kind are for example: DISTY® 125 (Geronazzo) and SOPROPHOR® CY 18 (Rhone Poulenc S.A.);

fatty acid (polyethoxyethyl) esters of the formula

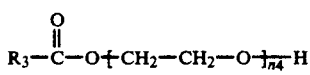

wherein $R_3$ is $C_8$-$C_{22}$alkyl or $C_{10}$-$C_{22}$alkenyl and $n_4$ is 2 to 50. These products are derived in particular from lauric acid, oleic acid and stearic acid. Such products are commercially available for example under the registered trademarks NONISOL® (Ciba-Geigy) or MRYJ® (ICI);

sorbitan polyethylene glycol ether fatty acid esters of the formula

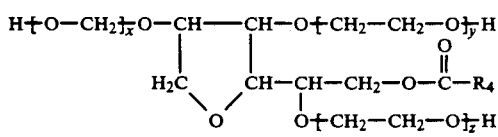

wherein $R_4$ is $C_8$-$C_{20}$alkyl and x, y and z are each 1 to 50, and the sum of $x+y+z$ is 20-150. Possible acid radicals $R_4$ are in particular the radicals of lauric acid, stearic acid, palmitic acid and oleic acid. Such products are also known as polysorbates and are commercially available for example under the registered trademark TWEEN® (ICI);

triglyceride polyethylene glycol ethers of the formula

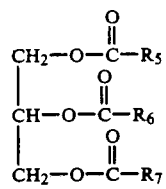

wherein $R_5$, $R_6$ and $R_7$ are the radical of the formula

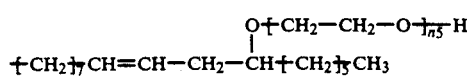

and each of $R_5$ and $R_6$ independently of the other is also $C_8$-$C_{20}$alkyl or $C_8$-$C_{20}$alkenyl, and $n_5$ is 3-100. Suitable acid radicals $R_5$CO— and $R_6$CO— containing $C_8$-$C_{20}$alkyl and $C_8$-$C_{20}$alkenyl groups are in particular the radicals of lauric acid, palmitic acid, stearic acid and oleic acid. A preferred representative of this type of surfactant is ethoxylated castor oil. Such products are commercially available under the registered trademark EMULSOGEN® (Hoechst AG);

fatty acid polyethoxyethylamides of the formula

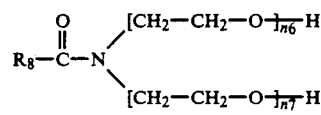

wherein $R_8$ is $C_8$-$C_{20}$alkyl, $C_8$-$C_{20}$alkenyl and $n_6$ and $n_7$ are each 1-25. Suitable acid radicals $R_8$CO— are in particular the radicals of lauric acid, oleic acid, palmitic acid and stearic acid. Products of this kind are commercially available for example under the registered trademarks AMIDOX® (Stephan Chemical Co.) and ETHOMID® (Armak Co.);

N-polyethoxyethylamines of the formula

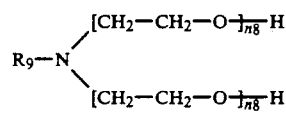

wherein $R_9$ is $C_8$-$C_{18}$alkyl or $C_8$-$C_{18}$alkenyl and $n_8$ is 1-15. The products derived from fatty amines, such as coconut fatty amine, oleylamine, stearylamine and tallow fatty amine, are particularly suitable. Such products are commercially available for example under the registered trademark GENAMIN® (Hoechst AG);

N,N,N'N'-tetra(polyethoxypolypropoxyethyl)ethylenediamines of the formula

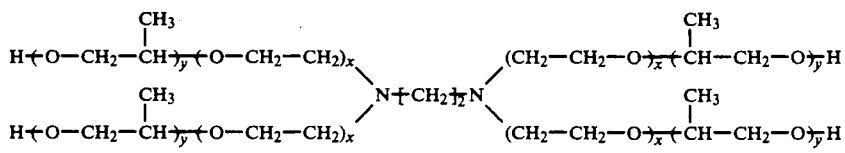

wherein x and y are each 2-50 and the sum of $x+y$ is 4-100. Products of this kind are commercially available, especially under the registered trademarks TERRONIL® and TETRONIC® (BASF Wyandotte Corp.);

alkyl polyethylene glycol/polypropylene glycol ethers of the formula

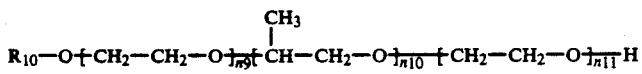

wherein $R_{10}$ is hydrogen, $C_8$–$C_{20}$alkyl or $C_8$–$C_{20}$alkenyl and $n_9$ and $n_{11}$ are each 2–200, $n_{10}$ is 10–80 and the sum of $n_9+n_{10}+n_{11}$ is 15–450. Particularly suitable products of this kind are for example polyethylene oxide/polypropylene oxide block polymers ($R_{10}=H$) commercially available under the registered trademark PLURONIC ® (BASF Wyandotte Corp.).

Preferred nonionic surfactants are ethylene oxide/propylene oxide block polymers (PLURONICS ®), N,N,N',N'-tetra(polyethoxypolypropoxyethyl)-ethylenediamines (TETRONICS ®), nonylphenol polyglycol ethers containing 10–20 ethylene oxide units, alkyl polyethylene glycol ethers which are derived from fatty alcohols (GENAPOL ®) and N-polyethoxyethylamines which are derived from fatty amines (GENAMIN ®). Particularly preferred nonionic surfactants are ethylene oxide/propylene oxide block polymers (PLURONICS ®).

The preferred process for the preparation of the aqueous suspensions of microcapsules of this inventions is carried out by first dissolving the anionic dispersant and the nonionic protective colloid and/or nonionic surfactant in water and then adding a solution of one or more polyisocyanates in a N-chloroacetylcyclohexeneamine of the formula I or in a mixture of a N-chloroacetylcyclohexeneamine of the formula I and a chloroacetanilide of the formula II, or a solution of a N-chloroacetylcyclohexeneamine of the formula I or a mixture of a N-choroacetylcyclohexeneamine of the formula I and a chloroacetanilide of the formula II in a water-immiscible solvent, and stirring the mixture efficiently until a homogeneous dispersion is obtained. With continuous stirring, one or more polyamines are added and stirring of the mixture is continued until the reaction of the polyamine with the isocyanate is completed. The polyamines can conveniently be added as aqueous solution.

The reaction time for the reaction of the polyisocyanate with the polyamine is normally from 2 to 30 minutes. The degree of conversion and the end of the reaction can be determined by titration of the free amine present in the aqueous phase.

The components required to form the capsule walls may generally be employed in an amount of 2.5 to 40% by weight, preferably 5 to 30% by weight, and most preferably 10 to 25% by weight, based on the material to be encapsulated. The material to be encapsulated may consist of a N-chloroacetylcyclohexeneamine of the formula I or of a mixture of a N-chloroacetylcyclohexeneamine of the formula I and a chloroacetanilide of the formula II, or of a solution of a N-chloroacetylcyclohexeneamine of the formula I or a mixture of a N-chloroacetylcyclohexeneamine of the formula I and a chloroacetanilide of the formula II in a water-immiscible solvent. The amount of components required to form the capsule wall in each specific case depends primarily on the wall thickness of the capsules to be prepared and also on the capsule size.

The diameter of the microcapsules produced according to the procedure described above is determined by the diameter of the droplets dispersed in the aqueous phase. The diameter of these droplets in turn depends on the stirring rate applied for the formation of the dispersion. High stirring rates will produce small droplets and the diameter of the droplets will increase with lowering of the stirring rate. However, the diameter of the microcapsules produced not only depends on the stirring rate but also on other factors, such as the type of stirrer employed, the volume to be stirred, the viscosity of the mixture etc. The parameters necessary for the production of microcapsules having a specific diameter can be easily determined experimentally.

The herbicidal compositions according to this invention advantageously contain microcapsules having a diameter within the range of 1 to 50 μm. Preferably, the diameter of the microcapsules is from 2 to 30 μm. For a given diameter of the microcapsules the thickness of the capsule wall depends on the amount of polymer formed by the wall-forming components, i.e. from the amount of polyisocyanate and polyamine used. For the microcapsules having a diameter within the range given above a polymer content of 2.5 to 40% by weight is suggested. Preferably, the microcapsules have a polymer content of 5 to 30% by weight and, most preferably, 10 to 25% by weight, based on the material to be encapsulated.

The release rate of the active ingredient can be influenced by the thickness of the capsule wall, the diameter of the capsules and by encapsulating an additional water-imiscible solvent together with the active substance. When dispersing the liquid phase to be encapsulated containing the polyisocyanate in water, the simultaneous use of an anionic dispersant and a nonionic protective colloid and/or nonionic surfactant prevents the sharp rise in viscosity that occurs particularly if an anionic dispersant alone is used, for example a ligninsulfonate. It is thus not only easier to carry out the process, but also simultaneously to achieve a more rapid and more complete reaction of polyisocyanate and polyamine, thereby substantially preventing the formation of undesirable by-products. Lowering the viscosity of the reaction mixture also leads to the formation of a finer dispersion at the same shearing force and thus to a reduction in the diameter of the capsules obtained. The capsule suspensions prepared by the process of this invention are stable and, even on prolonged storage, exhibit no formation of serum or sediment. Further, by appropriate choice of the kind and amount of the anionic and nonionic dispersants, the capsule suspensions obtainable in the process of this invention exhibit thixotropic properties and can therefore be brought in simple manner into a readily flowable state by shaking or stirring.

With the process described above it is possible to prepare aqueous suspensions of microcapsules that contain 100–700 g of microcapsules per liter. Preferably the suspensions contain 400–600 g of microcapsules per liter.

The suspensions of microcapsules obtainable in the process described above are directly ready for use. However, for transportation and storage they can be stabilised by the addition of further ingredients, such as surface-active agents, thickeners, antifoams and antifreeze agents. It is, however, also possible to seperate the microcapsules from the directly obtained suspension, for example by filtration or centrifugation, and either to dry or convert them once more into a suspension. The microcapsules which have been isolated from the suspension and dried are in the form of a flowable powder that has a virtually unlimited shelf of life.

The herbicidal compositions provided by the present invention have both a good initial activity and a good long term activity. This must be considered as surprising because according to common experience the microencapsulation of active substances is accompanied by a loss of initial activity.

In the following Examples which illustrate the invention more in detail the registered trademarks and other designations that are not self-evident denote the following products:

MDI is 4,4'-diphenylmethanediisocyanate
HMDA is 1,6-hexamethylenediamine
CS 500, CS 450, CS 400 and CS 300 denote the amount of active ingredient microencapsulated per litre (500 g/l, 450 g/l, 400 g/l or 300 g/l)
EC 250 and EC 480 denote the amount of active ingredient in conventional emulsion concentrates per litre (250 g/l or 480 g/l)

Anionic dispersants

Dispersant A: sodium salt of a condensate of naphthalenesulfonic acid with phenolsulfonic acid and formaldehyde, prepared according to Example A1.

Nonionic surfactants

PLURONIC ® F-108: ethylene oxide/propylene oxide block polymer of the formula $(EO)_x$—$(PO)_y$—$(EO)_z$, with mol wt of c. 16,000 and an ethylene oxide content of 80%, supplier BASF Wyandotte Corp.

Antaron ® P-904: Butylpolyvinylpyrrolidon with an average mol wt. of 1600, supplier: GAF Chem. Corp.

EXAMPLE A1: PREPARATION OF DISPERSANT A

Starting materials: 288 g (2.25 moles) of naphthalene, 144 g (1.53 moles) of phenol, 440 g (4.48 moles) of 100% sulfuric acid, 78.5 g (0.97 mole) of 37% aqueous formaldehyde solution, 370 g (4.4 moles) of 48% aqueous sodium hydroxide solution.

The naphthalene is melted in a stirred reactor and, after addition of sulfuric acid, the melt is heated for 4 hours to 120°-125° C. The phenol is then added and the temperature is kept for a further hour at 120°-125° C. The reaction vessel is subsequently evacuated to a pressure of 15 mbar and the temperature is increased slowly to 160° C. and kept for 3 hours while distilling off the water of reaction. The reaction mixture is cooled to 105°-110° C. and homogenised by stirring. The batch is then cooled to 90° C. by cautiously adding 200 g of ice, while maintaining the homogenity of the mixture by continual stirring. The formaldehyde solution is then added at 90°-95° C. over 1 hour and stirred for 3 hours at 95° C. A sample of the reaction mixture then forms with water a clear 5% solution and no longer smells of formaldehyde. The reaction mixture is then cooled to 80° C. by addition of 60 g of ice and 60 g of water. After addition of a further 180 ml of water, the reaction mixture is neutralised with about 230-250 ml of 48% sodium hydroxide solution at a temperature of 80° C. The pH of a 10% solution of a sample of the reaction mixture is about 6.5. The reaction mixture is then evaporated to dryness and the residue is granulated, affording 900 g of dispersant A in the form of water-soluble granules.

EXAMPLES FOR MICROENCAPSULATION OF N-CHLOROACETYL-N-ISOPROPYL-3,5 5(3)TRIMETHYLCYCLOHEX-1-EN-AMINE (TRIMEXACHLOR)

In the examples given hereinafter the average particle size is determined by the stirring rate.

The preparatory examples are performed by using a X20- or X40- high shear mixer purchased from YS-TRAL GmbH, D-7801 Ballrechten-Dottingen, the upper particle sizes are obtained using a conventional blade thrill. Depending on stirring rate and mixer type used, the particle sizes given can be obtained:

| stirring rate | particle size |
|---|---|
| X 20- or X40- high shear mixer | |
| 10 m/sec | 2 μm |
| 5 m/sec | 6 μm |
| blade thrill: | |
| 0,5 m/sec | 30 μm |

EXAMPLE H1: PREPARATION OF CS500 MICROCAPSULES OF TRIMEXACHLOR

1a. In a 250 ml glass beaker there are dissolved 0.8 g of dispersant A and 0.8 g of Pluronic F 108 in 71 g of deionised water and while stirring vigorously there is added a solution of 3.4 g of MDI in 80 g of trimexachlor. After about one minute, there is added further 1.4 g of HMDA (as 40% aqueous solution). Stirring is continued at a moderate rate for one hour, whereby the reaction mixture cools down to room temperature. According to the stirring rate, microcapsules of 2-30 μm are obtained.

1b. In a 250 ml beaker glass, there are dissolved 0.8 g of dispersant A and 0.8 g of Pluronic F 108 in 64 ml of deionised water and while stirring vigorously, a solution of 7.2 g MDI in 30 g of trimexachlor is added. After about one minute, there is further added 3.0 g HMDA as 40% aqueous solution. Stirring is then continued for one hour at moderate rate. According to the stirring rate, microcapsules of 2-30 μm are obtained.

1c. In a 250 ml beaker glass there are dissolved in 53 g of deionised water 1.6 g of dispersant A and 1.6 g of Pluronic F 108 while stirring vigorously there is added thereto first a solution of 14.9 g of MDI in 80 g of trimexachlor and after about one minute 6.2 g of HMDA (as 40% aqueous solution). Stirring is continued at a moderate rate for about one hour. According to the stirring rate microcapsules of 2 to 30 μm are obtained.

EXAMPLE H2: PREPARATION OF CS 450 MICROCAPSULES OF TRIMEXACHLOR

2a. To a solution of 0.9 g dispersant A and 1.8 g of Pluronic F 108 in 72.7 g of deionised water are added while stirring vigorously, first a soluiton of 11.6 g of MDI in 81 g of trimexachlor and after about one minute 4.8 g of HMDA (as 40% aqueous solution). The reaction mixture is then stirred at moderate rate for one hour. According to the stirring rate, microcapsules of 3 to 30 μm are obtained.

2b. To a solution of 0.9 g of dispersant A and 1.8 g of Pluronic F 108 in 56 g of deionised water are added while stirring vigorously, first a solution of 14.6 g of MDI in 72 g of trimexachlor and after about one minute 0.6 g of HMDA (in form of a 40% aqueous solution). Stirring is continued at a moderate rate for one hour. According to the stirring rate, microcapsules of 3 to 30 μm are obtained.

EXAMPLE H3: PREPARATION OF CS 400 MICROCAPSULES OF TRIMEXACHLOR

3a. To a solution of 0.8 g of dispersant A 0.8 g of Pluronic F 108 and 8 g of 1,2 Propyleneglycol in 14.4 g of deionised water are added while stirring vigorously, first a solution of 28 g of toluene and 7.2 g of MDI in 64 g of trimexachlcor and after about one minute 3.0 g of HMDA (as 40% aqueous solution). Stirring is continued for one hour at moderate rate. According to the stirring rate, microcapsules of 2 to 30 μm are obtained.

3b. To a solution of 0.8 g of dispersant A, 0.8 g of Pluronic F 108 and 8 g of 1,2 propyleneglycol in 46.2 g of deionised water are added, while stirring vigorously first a solution 28 g of toluene and 8.4 g of MDI in 64 g of trimexachlor and then after about one minute 1.8 g of ethylenediamine (as 40% aqueous solution). Stirring is then continued for one hour at moderate rate. According to the stirring rate when adding the trimexachor solution to the aqueous solution, microcapsules of 2 to 30 μm are obtained.

3c. To solution of 0.8 g of dispersant A and 0.8 g of Pluronic F 108 in 52.4 g of deionised water there are added, while stirring vigorously, first a solution of 28 g of toluene and 7.2 g of MDI in 64 g of trimexachlor and then, after about one minute 3.0 g of HMDA (as 40% aqueous solution). Stirring is continued at a moderate rate for one hour. According to the stirring rate, microcapsules of 2 to 30 μm are obtained.

3d. To a solution of 0.8 g of dispersant A and 0.8 g of Pluronic F 108 in 54.2 g of deionised water are added, while stirring vigorously, first a solution of 18 g of toluene and 8.4 g of MDI in 64 g of trimexachlor and then, after about one minute 1.8 g of ethylene diamine (as 40% aqueous solution). Stirring is then continued for one hour at a moderate rate. According to the stirring rate, microcapsules of 2 to 30 μm are obtained.

3e. To a solution of 0.8 g of dispersant A and 0.8 g of Pluronic F 108 in 56.8 g of deionised water are added, while stirring vigorously first a solution of 30.3 g of isophoron and 3.5 g of MDI in 64 g of trimexachlor and then, after about one minute 1.5 g of HMDA (as 40% aqueous solution). Stirring is continued for one hour at a moderate rate.

3f. To a solution of 0.8 g of dispersant a and 0.8 g of Pluronic F 108 in 56.8 g of deionised water are added, while stirring vigorously, first a solution of 30.3 g of 3,3,5-trimethylcyclohexanaone and 3.5 g of MDA in 64 g of trimexachlor and then, after about one minute, 1.5 g of HMDA (as 40% aqueous solution). Stirring is then continued at a moderate rate.

3g. To a solution of 0.8 g of Antaron P 904 and 8.0 g of 1.2 propyleneglycol in 45.2 g of deionised water are added, while stirring vigorously, first a solution of 28 g of toluene and 7.2 g of MDI in 64 g of trimexachlor, and then, after about one minute 3.0 g of HMDA (as 40% aqueous solution). Stirring is then continued at a moderate rate.

3h. To a solution of 8.0 g of Antonon P 904 and 8.0 g of 1,2 propyleneglycol in 48 g of deionised water are added, while stirring vigorously, first a solution of 28 g of toluene and 8.4 g of MDI in 64 g of trimexachlor and then, after about one minute 1.8 g of ethylenediamine (as 40% aqueous solution). Stirring is then continued for one hour at moderate rate.

3i. To a soluiton of 8.0 g of Antaron P 904 in 55 g of deionised water are added, while stirring vigorously, first a solution of 28 g of toluene and 8.4 g of MDI in 64 g of trimexachlor and then, after about one minute 1.8 g of ethylenediamine (as 40% aqueous solution). Stirring is then continued at a moderate rate.

EXAMPLE H4: PREPARATION OF CS 300 TRIMEXACHLOR MICROCAPSULES 4a. 5.0 g dispersant A and 5.0 g Pluronic F 108 are dissolved in 316.4 g deion. water and, with efficient stirring, a solution of 195 g toluene and 87,5 g MDI in 300 g Trimexachlor is added. After 1 minute 36.3 g HMDA (as 40% aqueous solution) are added and further stirred at a lower rate for one hour.

Depending on the stirring rate, during addition of the trimexachlor solution to the aqueous phase, one obtains microcapsules of 2 to 30 μm size.

4b. 7.5 g dispersant A and 7.5 g Pluronic F 108 are dissolved in 523 g deion. water and, with efficient stirring, a solution of 58.4 g MDI in 293 g toluene and 450 g Trimexachlor is added. After 1 minute 24.2 g HMDA (as 40% aqueous solution) are added and further stirred at a lower rate for one hour.

Depending on the stirring rate, during addition of the trimexachlor solution to the aqueous phase, one obtains microcapsules of 2 to 30 μm size.

4c. 7.5 g dispersant A and 7.5 g Pluronic F 108 are dissolved in 535 g deion. water and with, efficient stirring, a solution of 27.6 g MDI in 293 g toluene and 450 g trimexachlor is added. After 1 minute 11.5 g HMDA (as 40% aqueous solution) are added and further stirred at a lower rate for one hour.

Depending on the stirring rate, during addition of the trimexachlor solution to the aqueous phase, one obtains microcapsules of 2 to 30 μm size.

4d. 0.6 g dispersant A and 0.6 g Pluronic F 108 are dissolved in 52.8 g deion. water and, with efficient stirring, a solution of 20.6 g MDI in 15 g toluene and 36 g Trimexachlor is added. After 1 minute 2.3 g HMDA (as 40% aqueous solution) are added and further stirred at a lower rate for one hour.

Depending on the stirring rate, during addition of the trimexachlor solution to the aqueous phase, one obtains microcapsules of 2 to 30 μm size.

4e. 0.6 g dispersant A and 0.6 g Pluronic F 108 are dissolved in 53.8 g deion. water and, with efficient stirring, a solution of 12.9 g MDI in 15 g toluene and 36 g Trimexachlor is added. After 1 minute 0.1 g 1,4-diazabicyclo[2,2,2]octane (as 40% aqueous solution) are added. The mixture is then warmed to 45°–50° C. and further stirred at a lower rate for one hour.

Depending on the stirring rate, during addition of the trimexachlor solution to the aqueous phase, one obtains microcapsules of 2 to 30 μm size.

4f. 0.6 g dispersant A and 0.6 g Pluronic F 108 are dissolved in 61.6 g deion. water and, with efficient stirring, a solution of 3.0 g MDI in 15 g toluene, 1.0 g sebacic acid dichloride and 36.0 g Trimexachlor is added. After 1 minute 1.7 g HMDA (as 40% aqueous solution) are added and further stirred at a lower rate for one hour.

Depending on the stirring rate, during addition of the trimexachlor solution to the aqueous phase, one obtains microcapsules of 2 to 30 μm size.

4g. 0.6 g dispersant A and 0.6 g Pluronic F 108 are dissolved in 62.6 g deion. water and, with efficient stirring, a solution of 3.5 g MDI in 15 g toluene, 1.1 g sebacic acid dichloride and 36.0 g Trimexachlor is added. After 1 minute 1.1 g ethylenediamine (as 40% aqueous solution) are added and further stirred at a lower rate for one hour.

Depending on the stirring rate, during addition of the trimexachlor solution to the aqueous phase, one obtains microcapsules of 2 to 30 μm size.

EXAMPLE H5: PREPARATION OF MICROCAPSULES CONTAINING TRIMEXACHLOR/METOLACHLOR MIXTURES 5a. 1.6 g dispersant A, 8.0 g 1,2-propylenglycol and 1.6 g Pluronic F 108 are dissolved in a 250 ml beaker in 54 g water. With efficient stirring a solution of 40.0 g trimexachlor and 6.9 g MDI in 40.0 g metolachlor is added and it is further stirred until the desired particle size is reached. Then 2.8 g HMDA (as 40% aqueous solution) are added. Depending on the stirring rate microcapsules of 2 to 30 μm size are obtained.

The microcapsules prepared are of 10.0% polymer content, calculated on the amount of trimexachlor and metolachlor (CS 500 - microencapsulation). 5b. 1.6 g dispersant A, 8.0 g 1,2-propylenglycol and 1.6 g Pluronic F 108 are dissolved in a 250 ml beaker in 36.5 g water. With efficient stirring a solution of 40.0 g trimexachlor and 17.9 g MDI in 40.0 g metolachlor is added and it is further stirred until the desired particle size is reached. Then 7.4 g HMDA (as 40% aqueous solution) are added. Depending on the stirring rate microcapsules of 2 to 30 μm size are obtained.

The microcapsules prepared are of 26% polymer content, calculated on the amount of trimexachlor and metolachlor (CS 500 -microencapsulation).

5c. 1.6 g dispersant A and 1.6 g Pluronic F 108 are dissolved in a 250 ml beaker in 38.0 g water. With efficient stirring a solution of 56.0 g trimexachlor and 15.8 g MDI in 24.0 g metolachlor is added and it is further stirred until the desired particle size is reached. Then 6.5 g HMDA (as 40% aqueous solution) are added and it is further stirred for one hour. Depending on the stirring rate microcapsules of 2 to 30 μm size are obtained.

The microcapsules prepared are of 23% polymer content, calculated on the amount of trimexachlor and metolachlor (CS 500 -microencapsulation).

5d. 1.6 g dispersant A, 8.0 g 1,2-propylenglycol and 1.6 g Pluronic F 108 are dissolved in a 250 ml beaker in 38.2 g water. With efficient stirring a solution of 42.7 g trimexachlor and 15.0 g MDI in 21.3 g metolachlor and 16.0 g toluene is added and it is further stirred until the desired particle size is reached. Then 6.2 g HMDA (as 40% aqueous solution) are added. Depending on the stirring rate microcapsules of 2 to 30 μm size are obtained.

The microcapsules prepared are of 21% polymer content, calculated on the amount of trimexachlor, toluene and metolachlor (CS 400 -microencapsulation).

5e. 1.6 g dispersant A, 8.0 g 1,2-propylenglycol and 1.6 g Pluronic F 108 are dissolved in a 250 ml beaker in 38.2 g water. With efficient stirring a solution of 26.6 g trimexachlor and 15.0 g MDI in 53.4 g metolachlor is added and it is further stirred until the desired particle size is reached. Then 6.2 g HMDA (as 40% aqueous soluiton) are added and it is slowly stirred further. Depending on the stirring rate microcapsules of 2 to 30 μm size are obtained.

The microcapsules prepared are of 21% polymer content, calculated on the amount of trimexachlor and metolachlor (CS 500 -microencapsulation).

5f. 1.6 g dispersant A, 8.0 g 1,2-propylenglycol and 1.6 g Pluronic F 108 are dissolved in a 250 ml beaker in 54 g water. With efficient stirring a solution of 40.0 g trimexachlor and 3.5 g MDI in 40.0 g metolachlor is added and it is further stirred until the desired particle size is reached. Then 1.4 g HMDA (as 40% aqueous solution) are added. Depending on the stirring rate microcapsules of 2 to 30 μm size are obtained.

The microcapsules prepared are of 5.0% polymer content, calculated on the amount of trimexachlor and metolachlor (CS 500 -microencapsulation).

The date of microcapsules obtained according to examples 5a to 5f are summarizsed in table 1.

TABLE 1

| Example | content of AI [%] | Trimexachlor/ Metolachlor ratio | content of solvent [%] | Polymer content [%]* | capsules size [μm] |
|---|---|---|---|---|---|
| 5a | 50% | 1:1 | — | 10,8 | 2–30 |
| 5b | 50% | 1:1 | — | 24,0 | 2–30 |
| 5c | 50% | 2,3:1 | — | 22,0 | 2–30 |
| 5d | 40% | 2:1 | 20,0 | 21,0 | 2–30 |
| 5e | 50% | 1:2 | — | 21,0 | 2–30 |
| 5f | 50% | 1:1 | — | 5,0 | 2–30 |

*in relation to the whole capsular material

Biological examples

EXAMPLE B1 ACTIVITY AGAINST ECHINOCHLOA CRUS-GALLI, INITIAL- AND LONG-TERM-ACTIVITY (IN STERILIZED SOIL)

Plastic pots (50×30×10 cm) are filled with sterilized soil and, after treatment with the formulation of active agent to be investigated at the application rate given, are kept in the greenhouse. Immediately after application (test series I, determination of initial activity) or three weeks after application (test series II, determination of long term activity) seeds of Echinochloa crusgalli were sown onto the surface. The herbicidal activity is evluated 10 to 12 days after sowing by visual means (0=like untreated control, 100=100% herbicidal activity). Trimexachlor (N-Isopropyl-N-chloroacetyl-3,5,5(3)-trimethyl-cyclohex-1-en-amine) is tested in an EC 250 standard formulation (emulsifiable concentrate) and as CS 500 according to example 1a having an average partical size of 2 to 4 μm and a polymer content of 2,5 to 20%.

This formulation of trimexachlor are compared with a commercially available emulsifiable concentrate (EC 480) and a commercially available microencapsulated formulation (MT 480) of alachlor (N-Chloroacetyl-N-methoxymethyl-2,6-diethylaniline) in relation to their initial- and long-term activity.

The results are summarized in table 2:

TABLE 2

| Active ingredient formulation | Application [kg AI/ha] | Test series I [immediately after application] | Test series II [3 weeks after application] |
|---|---|---|---|
| Trimexachlor | 0,25 | 99 | 0 |
| EC 250 | 0,5 | 100 | 5 |
| | 1,0 | 100 | 60 |

TABLE 2-continued

| Active ingredient formulation | | Application [kg AI/ha] | Test series I [immediately after application] | Test series II [3 weeks after application] |
|---|---|---|---|---|
| | | 2,0 | 100 | 95 |
| Trimexachlor CS 500 | 2,5%[1] 2–4 μm[2] | 0,25 | 99 | 20 |
| | | 0,5 | 100 | 35 |
| | | 1,0 | 100 | 65 |
| | | 2,0 | 100 | 99 |
| Trimexachlor CS 500 | 5%[1] 2–4 μm[2] | 0,25 | 100 | 20 |
| | | 0,5 | 100 | 35 |
| | | 1,0 | 100 | 89 |
| | | 2,0 | 100 | 97 |
| Trimexachlor CS 500 | 10%[1] 2–4 μm[2] | 0,25 | 100 | 35 |
| | | 0,5 | 100 | 55 |
| | | 1,0 | 100 | 89 |
| | | 2,0 | 100 | 100 |
| Trimexachlor CS 500 | 20%[1] 2–4 μm[2] | 0,25 | 95 | 70 |
| | | 0,5 | 99 | 90 |
| | | 1,0 | 100 | 100 |
| | | 2,0 | 100 | 100 |
| Alachlor EC 480[3] | | 0,25 | 97 | 40 |
| | | 0,5 | 99 | 45 |
| | | 1,0 | 100 | 97 |
| | | 2,0 | 100 | 99 |
| Alachlor MT 480[4] | | 0,25 | 30 | 65 |
| | | 0,5 | 80 | 94 |
| | | 1,0 | 93 | 95 |
| | | 2,0 | 100 | 100 |

[1]Polymer content
[2]Particle size
[3]Emulsifiable concentrate commercially obtainable as Lasso ® of Monsanto Comp. USA (AI content 480 g/l)
[4]Microencapsulated formulation commercially obtainable as Micro-Tech ™ Lasso ® of Monsanto Comp. USA (AI content 480 g/l).

EXAMPLE B2 LONG-TERM-ACTIVITY AGAINST ECHINOCHLOA CRUS-GALLI IN NON-STERILE SOIL

Analogous to example B1 an EC 250 standard formulation of trimexachlor, a CS 400 formulation of trimexachlor according to example H3 and two metolachlor/-trimexachlor formulations according to example H5 are tested. Nonsterile soil is used in place of sterilized soil. The plants are sown 30 days after application and the herbicidal activity is evaluated 10 to 12 days after sowing.

The results are summarized in table 3:

TABLE 3

| | Formulations tested | | |
|---|---|---|---|
| | | Metolachlor/Trimexachlor 1:1 | |
| Application rate kg AS/ha | Trimexachlor EC 250 | CS 500 5% Polymer content | CS 500 10% Polymer content |
| | CS 400 | | |
| 0,25 | 0   0 | 90 | 35 |
| 0,5 | 0   10 | 90 | 60 |
| 1,0 | 0   95 | 98 | 98 |

What is claimed is:

1. A herbicidal composition which comprises an aqueous suspension of microcapsules having a capsule wall of polyurea and encapsulating a herbicidally active N-chloroacetylcyclohexeneamine of the formula I

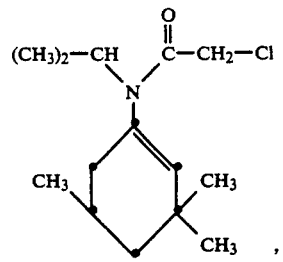

2. A herbicidal composition according to claim 1, wherein the microcapsules encapsulate in addition to a herbicidally active N-chloroacetylcyclohexeneamine of the formula I 0.25–0.75 parts per weight of a water-imiscible solvent per part of the N-chloroacetylcyclohexeneamine of the formula I.

3. A herbicidal composition according to claim 2, wherein the waterimiscible solvent is selected from the group comprising aliphatic or aromatic hydrocarbons, a cyclic ketones or a halogenated hydrocarbons.

4. A herbicidal composition according to claim 3, wherein the waterimiscible solvent is selected from the group consisting of hexane, cyclohexane, benzene, toluene, xylene, mineral oil, kerosene, cyclohexanone, methylene chloride, chloroform, chlorobenzene, o-dichlorobenzene or a mixture of mono- and polyalkylated aromatics.

5. A herbicidal composition according to claim 1, wherein the microcapsules have a polymer content of 2.5 to 40% by weight based on the material to be encapsulated.

6. A herbicidal composition according to claim 5, wherein the microcapsules have a polymer content of 5 to 30% by weight based on the material to be encapsulated.

7. A herbicidal composition according to claim 5, wherein the microcapsules have a polymer content of 10 to 25% by weight based on the material to be encapsulated.

8. A herbicidal composition according to claim 1 containing 100–700 g of microcapsules per liter.

9. A herbicidal composition according to claim 8 containing 400–600 g of microcapsules per liter.

10. A herbicidal composition according to claim 1, wherein the microcapsules at a diameter within the range 1 to 30 μm.

11. A herbicidal composition according to claim 10, wherein the microcapsules have a diameter of from 2 to 30 μm.

12. A herbicidal composition which comprises an aqueous suspension of microcapsules having a capsule wall of polyurea and encapsulating a herbicidally active N-chloroacetylcyclohexeneamine of the formula I

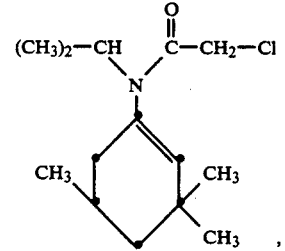

wherein the capsule wall of polyurea further contains up to 30% by weight of a polyamide.

* * * * *